United States Patent [19]

Daigle et al.

[11] Patent Number: 5,253,653
[45] Date of Patent: Oct. 19, 1993

[54] FLUOROSCOPICALLY VIEWABLE GUIDEWIRE FOR CATHETERS

[75] Inventors: James B. Daigle, Worcester; Richard M. DeMello, Acton; Bruce W. Flight, Melrose, all of Mass.

[73] Assignee: Boston Scientific Corp., Watertown, Mass.

[21] Appl. No.: 786,061

[22] Filed: Oct. 31, 1991

[51] Int. Cl.⁵ .............................................. A61B 5/00
[52] U.S. Cl. .................................... 128/772; 128/657; 604/164; 604/280
[58] Field of Search .................. 128/657, 772; 604/95, 604/164, 280, 282; 606/192

[56] References Cited

U.S. PATENT DOCUMENTS

| | | | |
|---|---|---|---|
| 4,538,622 | 9/1985 | Samson et al. | 128/657 |
| 4,554,929 | 11/1985 | Samson et al. | 128/772 |
| 4,763,647 | 8/1988 | Gambale | 128/772 |
| 4,773,432 | 9/1988 | Rydell | 128/772 |
| 4,932,419 | 6/1990 | Toledo | 128/772 |
| 5,063,935 | 11/1991 | Gambale | 128/772 |
| 5,065,769 | 11/1991 | Toledo | 128/772 |
| 5,069,217 | 12/1991 | Fleischhacker | 128/772 |
| 5,095,915 | 3/1992 | Engelson | 128/657 |
| 5,111,829 | 5/1992 | Toledo | 128/772 |
| 5,165,421 | 11/1992 | Fleischhacker et al. | 128/772 |
| 5,174,302 | 12/1992 | Palmer | 128/772 |

FOREIGN PATENT DOCUMENTS 2180277  7/1990  Japan .................................. 128/657

Primary Examiner—Stephen C. Pellegrino
Assistant Examiner—Glenn Dawson

[57] ABSTRACT

A guidewire assembly for measuring the size of occlusions in blood vessels which includes a guidewire having a flexible, distal end disposable in a blood vessel. The guidewire has a core wire disposed within it which extends to the distal tip. A linear array of radiopaque markers is disposed adjacent the distal tip of the core wire. The markers are spaced from each other at predetermined distances, whereby to enable the user to accurately measure the size and diameter of occlusions in blood vessels using radiological techniques.

9 Claims, 2 Drawing Sheets

FLUOROSCOPICALLY VIEWABLE GUIDEWIRE FOR CATHETERS

FIELD OF THE INVENTION

The present invention relates to an improved catheter for treating a tissue target site which is accessible by a tortuous path through small vessels. More specifically, the present invention relates to a guidewire for a catheter, the guidewire having a core wire disposed therein. The catheter of the present invention can be inserted into the small vessels and can enable a physician to identify the magnitude of the target site through radiography.

DESCRIPTION OF THE PRIOR ART

Blood vessels and other tubular structures in the body often undergo narrowing and the formation of obstructions. These vessels can be restored to their original diameters by various medical means, especially through the use of balloon catheters. A balloon catheter dilates the vessels by expanding a balloon on the distal end portion of a catheter tube. The balloon tip is inflated by the physician when it is placed within an occlusion of a blood vessel and dilates the vessel to form a clear path therethrough. The catheter and the balloon are single piece units with the balloon being a thin catheter wall portion of predetermined shape and size. A guidewire is disposed within the catheter to stiffen it and to provide guidance to the site of the occlusion. The guidewire can also be used to stretch the balloon lengthwise in order to reduce the diameter so that it can be introduced through the obstructed area. Guidewires usually are made of radiopaque material so that their precise location can be identified during a surgical procedure through fluoroscopic viewing.

Use of x-ray imaging to view the guidewire, however, does not always identify the extent of the occlusion. Frequently there is a need to identify the length and thickness of the occlusion so that the physician can utilize the correct balloon size during the surgery.

In the prior art, the length and thickness of the occlusion is frequently measured by incrementally spaced marker bands on the outside of the catheter itself. Catheters with marker bands frequently are limited in that they cannot always be positioned directly in the vessel or in a region of the vessel where the occlusion is located. Special catheters for sizing occlusions in vessels have been developed but they require multiple catheter use and exchanging one for another.

Exemplary of markers used on guidewires in the art is the balloon catheter disclosed by LeVeen, U.S. Pat. No. 4,448,195, in which a radiopaque wire is mitered by machining it at predetermined locations. Miter cuts are used to measure distances on fluoroscopic images since they can be identified on a screen or film. Additionally, the reference teaches banding the outer sleeve of the catheter at both ends of the balloon to indicate the balloon's position to the physician performing the surgery. We have found that mitering of the guidewire and banding of the sleeve is not the best solution to obtaining views of the size and shape of arterial occlusions. The miter cuts cannot be seen easily on x-ray images, however, and they introduce weak points in the guidewire which makes it more breakable. Banding is less than desirable because the bands increase the diameter of the catheter and make insertion and use more difficult. Also exemplary of indicia disposed on the guidewire is the patent to Gambale et al, U.S. Pat. No. 4,922,924. The patent discloses a bifilar arrangement where radiopaque and radiotransparent filaments are wrapped on a mandril to form a bifilar coil which provides radiopaque and radiotransparent areas on the guide wire.

The U.S. Pat. No. 3,978,863 to Fettel et al, discloses the use of beads made of radiopaque materials to indicate the location of the tip of the catheter and the expandable balloon at the tip. We have found that the beads add bulk to the catheter and can make the insertion process more difficult.

SUMMARY OF THE INVENTION

According to the present invention, we have invented a novel, flexible and shapeable guidewire for a catheter. The guidewire of our invention has a radiopaque tip disposed at its distal end and a core wire is disposed within the guidewire. Radiopaque markers are disposed on the core wire in a gauging section located at the distal end of the guidewire to provide easily identifiable reference points for observation of the length and thickness of the occlusion under study. The distal end of the core wire is disposed in predetermined registration with an inner surface of the tip and a linearly arranged array of radiopaque markers are disposed on the distal end of the core wire and are spaced from each other at predetermined distances. Since an image of the tip of the guidewire can be seen on x-ray images and since the location of each of the markers is known and can be seen relative to the tip, the size and shape of occlusions being studied can be measured. When the markers are disposed on the core wire of the guidewire, we have found that the disposition of the markers does not add to the diameter of the catheter thereby enabling the physician to easily and safely insert the catheter into a blood vessel.

In the present invention, the guidewire has features which permit it to be used as a gauging tool having an internal core wire that is tapered and having a portion of reduced diameter at its distal end to receive an array of radiopaque markers. These markers may be radiopaque materials such as gold, silver, platinum, tantalum or other radiopaque, biocompatible materials.

The markers preferably are in the form of rings. The outer diameter of each ring is equal to or less than the diameter of the main body of the core wire at its gauging section but greater than the diameter of the core wire at its distal end. The inner diameter of each ring, that is the hole, may be substantially the same as the distal or gauging end of the core wire so that it can be fitted on to the gauging end. In the preferred embodiment the hole is larger than the core wire to provide a slip fit thereon.

Many ways can be used to make the markers. For example, radiopaque wire can be wound on a mandril that has a diameter slightly less than the diameter of the wire at the gauging section. The coil is then sliced into units of predetermined lengths. Radiopaque plastic tubing can be cut into segments or the markers can be formed of brazed or soldered material on the core wire.

The size, shape and location of each of the markers is highly important. Such dimensions and relationships enable the user to accurately gauge the area being measured with the guidewire gauging tool in closer proximity to the occlusion being measured. Moreover, the guide wire can be used to advance other devices such as an angioplastic balloon catheter or stent device, thereby minimizing the need to exchange catheters or guidewires. Because no significant bumps are on the gauging section, the guidewire can be easily withdrawn from a catheter that may house it.

DESCRIPTION OF THE PREFERRED EMBODIMENT

Figure 1:
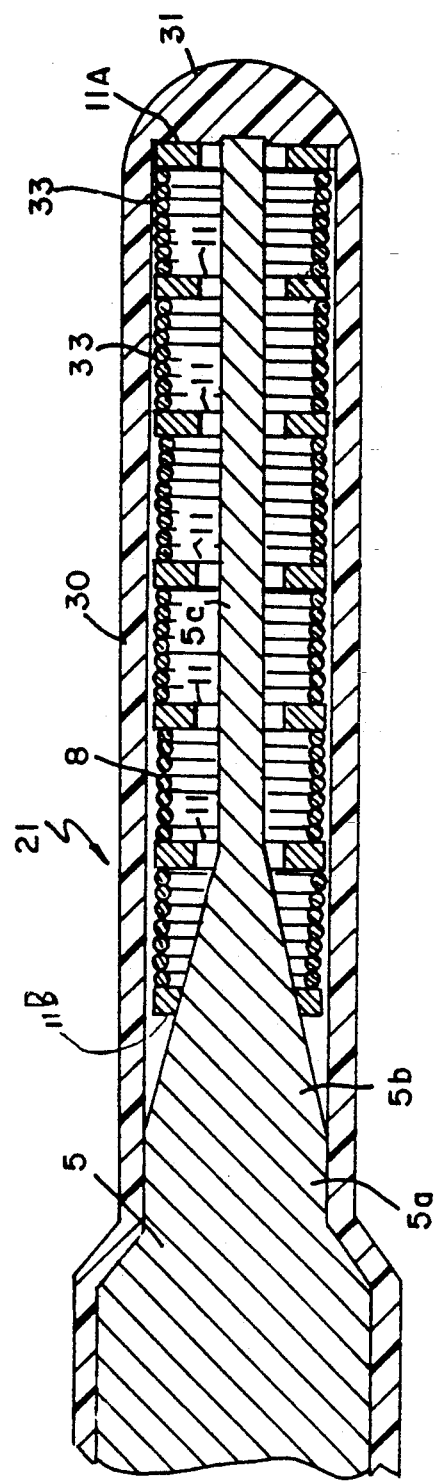
FIG. 1 is a side elevational view, partially in cross-section of a guidewire in a plastic jacket according to one embodiment of the present invention. The view shows the disposition of radiopaque markers on a core wire in the guidewire.

Referring to FIG. 1 of the drawing, a core wire 5 is shown with a distal end that forms a gauging section 5c which is necked down or tapered from a larger diameter body section 5a to the smaller diameter section 5c. The reduction in diameter is provided at a necked down section 5b. The diameter of the body section 5a of core wire 5 is about 0.020" and the diameter of the gauging section 5c is between about 0.002 to 0.006" with 0.004" being preferred.

An series of radiopaque rings which serve as markers 11 is disposed on the gauging section 5c of the core wire 5. These radiopaque markers 11 are made as described above and are arranged in a predetermined spaced relationship to each other and also relative to a distal marker 11A and a proximal marker 11B. The distal marker 11A and the proximal marker 11B can be of a construction that is identical to the other markers, differing only by their positions on the core wire 5 and that they are fixedly attached thereto. The distal marker 11A and the proximal marker 11B are each attached to the gauging section 5c and the tapered section 5b of the core wire with a suitable adhesive or weld. The intermediate markers 11, that is those between distal marker 11A and proximal marker 11B, are not attached to the core wire and serve as supports for an arrangement of helical coils 8 which are disposed between them. The markers 11 are spaced from each other by one centimeter or by such other spacing as desired.

In the embodiment of this Figure, the coils 8 are formed of flexible wire coils which are preferably made of single layer windings of a suitable radiotransparent material such as stainless steel. The wire of the coils 8 has a diameter less than about 0.0075". The outer diameter of the coils 8 is preferably less than about 0.045". As shown, the markers 11 of this embodiment also have an outer diameter of about 0.045" and the coils 8 are about 1 cm. long whereby to hold the coils 8 between them at spacings of 1 cm. Since the distal marker 11A and the proximal marker 11B are attached to the gauging section 5c and the tapered section 5b respectively of the core wire, the markers 11 disposed therebetween are held in place at 1 cm. intervals, but can shift about somewhat because of the flexibility of the coils 8 so as to compensate for the twists and turns the device will take while it is being inserted into a vessel.

The markers, the core wire and the coils are disposed within a radiotransparent jacket 30 that includes a distalmost hemispherical tip 31. The jacket 30 covers the entire assembly which includes the core wire, the coils 8 and the markers 11 to encapsulate that entire assembly. The jacket 30 can be heat formed (shrunk) over the entire assembly to encapsulate it. The jacket 30 can be made from any of the well known soft, biocompatible plastics used in the catheter art such as Percuflex, a trademarked plastic manufactured by Boston Scientific Corporation of Watertown Massachusetts. The wall thickness of the jacket 30 can be between about 0.003" and 0.008". When the catheter is inserted into a patient, the distal marker 11A will be identifiable in an X-ray, as will each of the other markers in the assembly. They can be formed of the well known radiopaque materials such as gold, platinum or tantalum.

Figure 2:
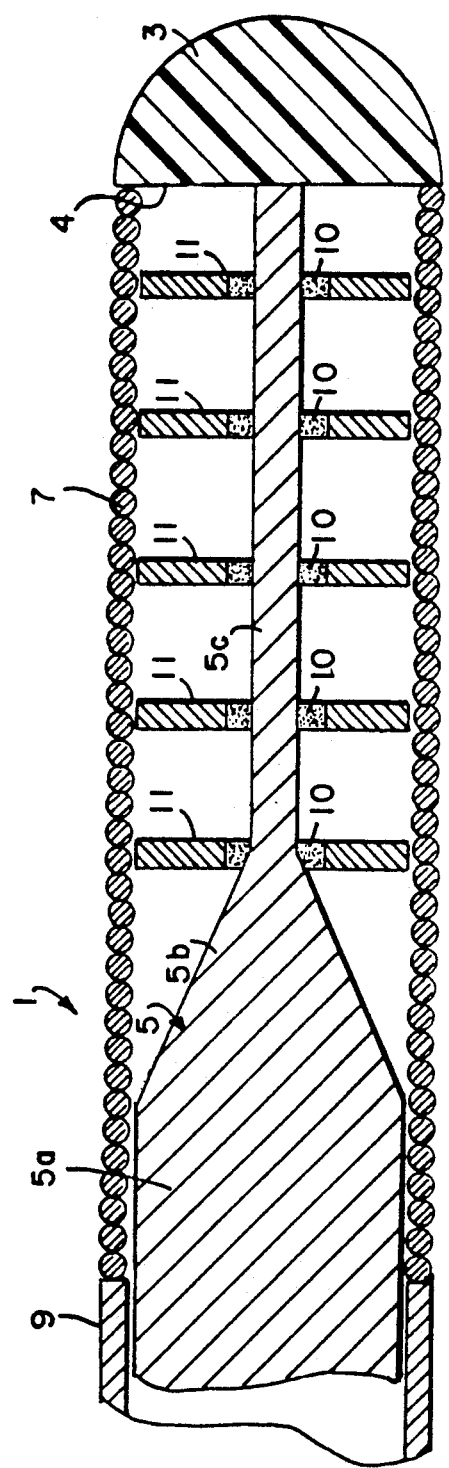
FIG. 2 is a view of another embodiment of the device according to the present invention.

Referring to FIG. 2 of the drawing, a guidewire assembly 1 is shown which includes a radiopaque tip 3. The tip 3 has a hemispherical shape and is formed of a radiopaque material such as platinum or gold. Tip 3 has a flat inner surface 4 which establishes a reference point for the array of markers 11, as will be discussed hereinafter.

The distal end of a coil 7 is attached to the periphery of the inner surface 4 of the tip 3 by welding, braising or soldering. The proximal end of the coil 7 is joined to a plastic jacket 9 also by welding or an adhesive, which jacket 9 is heat shrunk to the core wire 5a.

In this embodiment, the dimensions and the shape of the core wire 5 are the same as has been described above.

As with the embodiment of FIG. 1, an array of radiopaque markers 11 are disposed upon the gauging section 5c of the core wire 5. These radiopaque markers 11 are arranged in a predetermined spaced relationship to each other and also relative to the inner surface 4 of tip 3. The markers 11 are spaced from each other by about one centimeter and the spacing between the distal end of core wire 5 and the first radiopaque marker 11 is also about one centimeter. Other appropriate spacings may be established, as desired. Each of the markers 11 can be disposed on the gauging section 5c with an adhesive, or by welding, soldering or brazing. Alternatively, for example, the markers can be made by metallurgically plating successive layers on the gauging section 5c as coatings until the desired ring thickness is attained.

In this embodiment, the outer annular peripheral surfaces of the markers 11 are free to move within the inside of the coil 7. The inner and outer diameters of the jacket 9 approximate the inner and outer diameters of the coil 7.

If desired with either of the embodiments, the spaces between the markers 11 can be filled with a flexible, rubbery material 12 to help keep the markers in place. Exemplary of the rubbery materials that can be used are latex or urethane. Disposition of the rubbery material in between the markers can be accomplished by techniques well known to the art.

It is apparent that modifications and changes may be made within the spirit and scope of the present invention. It is our intention, however only to be limited by the scope of the appended claims.

As our invention we claim:

1. A fluoroscopically viewable guidewire for a catheter to measure the size and shape of occlusions in a blood vessel, said guidewire comprising:
   a core wire having a flexible distal end formed of a body section which tapers into a gauging section;
   a proximal marker means, a distal marker means and at least one intermediate marker means, each of said marker means being radiopaque and linearly disposed on said gauging section, said marker means being spaced from each other at a predetermined distance; and a helical coil of radiotransparent flexible wire surrounding at least the gauging section of said core wire.

2. The guidewire according to claim 1 wherein said marker means are rings disposed on said gauging section of said core wire, said rings having outer diameters that are no greater than the diameter of said body section of the core wire.

3. The guidewire according to claim 2 wherein the diameter of the core wire in the gauging section is less then about half the diameter of the core wire in the body section.

4. The guidewire according to claim 1 wherein spaces between the marker means are filled with a flexible rubbery mass.

5. A fluoroscopically viewable guidewire for a catheter to measure the size and shape of occlusions in a blood vessel, said guidewire comprising:
- a core wire having a flexible distal end formed of a body section tapering into a gauging section;
- a proximal marker ring, a distal marker ring and at least one intermediate marker ring disposed between said proximal and distal marker rings, each of said marker rings being radiopaque and linearly disposed on said gauging section, the diameter of said marker rings being substantially the same as the diameter of said body section, said marker rings being spaced from each other at predetermined distances, and
- a helical coil of radiotransparent flexible wire surrounding at least the gauging section of said core wire.

6. The guidewire according to claim 5 wherein the diameter of the core wire in the gauging section is less then about half the diameter of the core wire in the body section.

7. A fluoroscopically viewable guidewire for a catheter to measure the size and shape of occlusions in a blood vessel, said guidewire comprising:
- a guidewire including a core wire, said core wire terminating in a flexible distal end, said core wire extending along the length of said guidewire, the distal end of said core wire forming a gauging section, the diameter of said core wire being less at the gauging section than elsewhere on said core wire;
- a proximal marker, a distal marker and at least one intermediate marker disposed between said proximal and distal markers, each of said markers being radiopaque and linearly disposed on said gauging section, the outer diameters of said markers being equal to or less than the diameter of any part of said core wire, and
- a helical coil of radiotransparent flexible wire surrounding said distal end including the gauging section of said core wire and said markers.

8. The guidewire according to claim 7 wherein spaces between the markers is filled with a flexible rubbery mass.

9. The guidewire according to claim 7 wherein the gauging section of said core wire is truncated to less then about half the diameter of the guidewire so as to receive said markers.

* * * * *